(12) United States Patent
Matsuo et al.

(10) Patent No.: US 6,255,522 B1
(45) Date of Patent: Jul. 3, 2001

(54) PROCESS FOR REDUCING α-AMINO KETONES

(75) Inventors: Kazuhiko Matsuo; Shingo Matsumoto, both of Himeji; Kenji Inoue, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/230,887

(22) PCT Filed: Jun. 3, 1998

(86) PCT No.: PCT/JP98/02444

§ 371 Date: Sep. 29, 1999

§ 102(e) Date: Sep. 29, 1999

(87) PCT Pub. No.: WO98/55452

PCT Pub. Date: Dec. 10, 1998

(30) Foreign Application Priority Data

Jun. 3, 1997 (JP) .................................................. 9-162005
Jul. 29, 1997 (JP) .................................................. 9-219287

(51) Int. Cl.$^7$ ...................... C07C 271/14; C07C 321/28
(52) U.S. Cl. ................... 560/9; 560/17; 560/29; 568/305; 568/306; 568/307; 568/704; 568/705; 568/713
(58) Field of Search ..................... 568/305, 306, 568/307, 704, 705, 713; 560/9, 17, 29

(56) References Cited

FOREIGN PATENT DOCUMENTS

| 0 827 943 A1 | 3/1998 | (EP) . |
| 0 969 000 A1 | 1/2000 | (EP) . |
| WO98/11057 | 3/1998 | (WO) . |

OTHER PUBLICATIONS

Akamanchi et al, Truly Catalytic Meerwein–Ponndorf–Verley (MPV) Reduction, Tetrahedron Letters, vol. 36, No. 28, pp. 5085–5088, 1995.
Akamanchi et al, Aluminium Isopropoxide—TFA, a Modified Catalyst for Highly Accelerated Meerwein–Ponndorf–Verley (MPV) Reduction, Tetrahedron Letters, vol. 36, No. 20, pp. 3571–3572, 1995.
Akamanchi et al, Diisopropoxyaluminium Trifluoroacetate: A New off the Shelf Metal Alkoxide Type Reducing Agent for Reduction of Aldehydes and Ketones, Synlett, Apr. 1997, pp. 371–372.
Kow et al, Rate Enhancement of the Meerwein–Ponndorf–Verley–Oppenhauer Reaction in the Presence of Proton Acids, J. Org. Chem., vol. 42, No. 5, 1977, pp. 826–827.

Database CAPLUS on STN, Acc. No. 1994:654933, Cha et al., 'Reaction of dipyrrolidinoaluminum hydride in THF with selected organic compounds containing representative functional groups.' Bull. Korean Chem. Soc. (1994), 15(8), pp. 644–649. (abstract).*
Database CAPLUS on STN, Acc. No. 1994:243631, Cha et al., 'Reaction of bis (diethylamino)aluminum hydride in THF with selected organic compounds containing representative functional groups.' Bull. Korean Chem. Soc. (1994), 15(2), pp. 132–138. (abstract).*

* cited by examiner

*Primary Examiner*—Johann Richter
*Assistant Examiner*—Brian J. Davis
(74) *Attorney, Agent, or Firm*—Connolly Bove Lodge & Hutz

(57) ABSTRACT

The present invention has its objects to provide a method for reducing α-aminoketone derivatives under mild conditions with high stereoselectivity. This invention is a method for reducing α-aminoketone which comprises reacting an a-aminoketone derivative of general formula (1) with a compound prepared from an organoaluminum compound of general formula (4), a sulfonic acid derivative of general formula (5), and an alcohol compound of general formula (6) to give an α-aminoalcohol derivative of general formula (7)

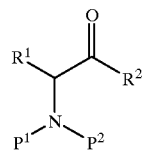

(1)

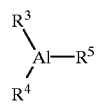

(4)

$R^6SO_3H$ (5)

$R^7OH$ (6)

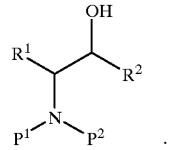

(7)

20 Claims, 1 Drawing Sheet

PROCESS FOR REDUCING α-AMINO KETONES

FIELD OF THE INVENTION

This application is a 371 of PCT/JP98/02444 filed Jun. 3, 1998.

The present invention relates to a method for stereoselectively reducing α-aminoketone derivatives, in particular α-aminohaloketorle derivatives.

The reduction products, namely α-aminoalcohol derivatives, in particular α-aminohalohydrin derivatives, are compounds useful as intermediates for the production of medicinal compounds, for example HIV protease inhibitors (Japanese Kokai Publication Hei-8-99959: Japanese Kokai Publication Hei-5-170722).

BACKGROUND ART

Reduction of carbonyl compounds is a very important technology in various fields, inclusive of the production of medicinal compounds and agrochemicals, and various methods have been utilized to answer respective specific purposes. Among them, the technology of converting optically active α-aminoketone derivatives to α-aminoalcohol derivatives by stereoselective reduction is required to be high in operability and efficient for industrialization since such α-aminoalcohol derivatives having an erythro configuration are important as intermediates of anti-HIV drugs, among others.

The "erythro" form means an isomer in which the amino group and hydroxy group bound to the adjacent carbon atoms have the relative configuration shown below. In the following formula, $Z_1$ and $Z_2$ represent the remaining chemical structure moieties.

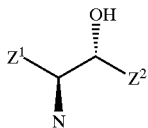

A prior art technology for reducing α-aminoketone derivatives comprises, for example, reducing them with diisobutylaluminum hydride (DIBAH), sodium borohydride, lithium tri-secondary-butylborohydride (L-Selectride) or the like at −78° C. [Tetrahedron Letters, 36, 5453 (1995)].

The reduction technology using DIBAH is excellent in reactivity and economy and is a very useful method from the( industrial viewpoint. This method is used in reducing, for example, α-aminochloroketone derivatives derived from leucine. When said α-aminochloroketone derivatives are reduced with DIBAH at −78° C., the erythro forms can be obtained preferentially with a diastereomer excess of about 75%.

However, this method requires an extremely low temperature of −78° C. for achieving high selectivity.

In Japanese Kokai Publication Hei-8-99959, a technology is disclosed which uses an aluminum trialkoxide as the reducing agent.

However, the technology disclosed in the above publication requires heating at a temperature not lower than 50° C. to raise the rate of reaction although the stereoselectivity is high. Thus, said technology still has problems to be solved; for instance, it is not suited for reducing thermally unstable substrates. Therefore, a practical technology has been demanded by which carbonyl compounds, in particular optically active α-aminoketone derivatives can be converted to erythro-form α-aminoalcohol derivatives by stereoselective reduction under mild conditions.

DISCLOSURE OF THE INVENTION

In the light of the above mentioned state of things, it is an object of the present invention to provide a method for reducing α-aminoketone derivatives, in particular α-aminohaloketone derivatives, under mild conditions to give α-aminoalcohol derivatives, in particular α-aminohalohydrin derivatives, with high stereoselectivity.

The present invention lies in a method for reducing α-aminoketones which comprises reacting an α-aminoketone derivative of the general formula (1);

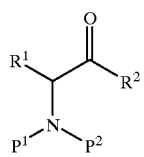

(1)

wherein $R^1$ represents one member selected from the group consisting of a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms, and a hydrogen atom: $R^2$ represents either a group of the general formula (2);

$$CH_nX_{3-n} \quad (2)$$

wherein X represents a halogen atom and n represents an integer of 0 to 2, or a group of the general formula (3);

(3)

wherein Y represents one member selected from the group consisting of an alkoxyl group, an aralkyloxyl group, a substituted or unsubstituted amino group, and an alkylthio group, $P^1$ and $P^2$ each independently represents a hydrogen atom or an amino-protecting group, exclusive of the case where $P^1$ and $P^2$ are the same and each represents a hydrogen atom, with a compound prepared from an organoaluminum compound of the general formula (4);

(4)

wherein $R^3$, $R^4$ and $R^5$ each independently represents a substituted or unsubstituted alkyl group containing 1 to 10 carbon atoms, or a hydrogen atom, on condition that at most one of $R^1$, $R^4$ and $R^5$ represents a hydrogen atom, a sulfonic acid derivative of the general formula (5);

$$R^6SO_3H \quad (5)$$

wherein R⁶ represents one member selected from the group consisting of a substituted or unsubstituted alkyl group containing 1 to 10 carbon atoms, a substituted or unsubstituted aralkyl group containing 7 to 20 carbon atoms, and a substituted or unsubstituted aryl group containing 6 to 20 carbon atoms, and an alcohol compound of the general formula (6):

R⁷OH  (6)

wherein R⁷ represents a substituted or unsubstituted, primary or secondary alkyl group containing 1 to 20 carbon atoms, or a substituted or unsubstituted, primary or secondary aralkyl group containing 7 to 20 carbon atoms, to give an α-aminoalcohol derivative of the general formula (7):

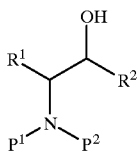

(7)

wherein R¹, R², P¹ and P² are as defined above.

DETAILED DESCRIPTION OF THE INVENTION

Figure 1:
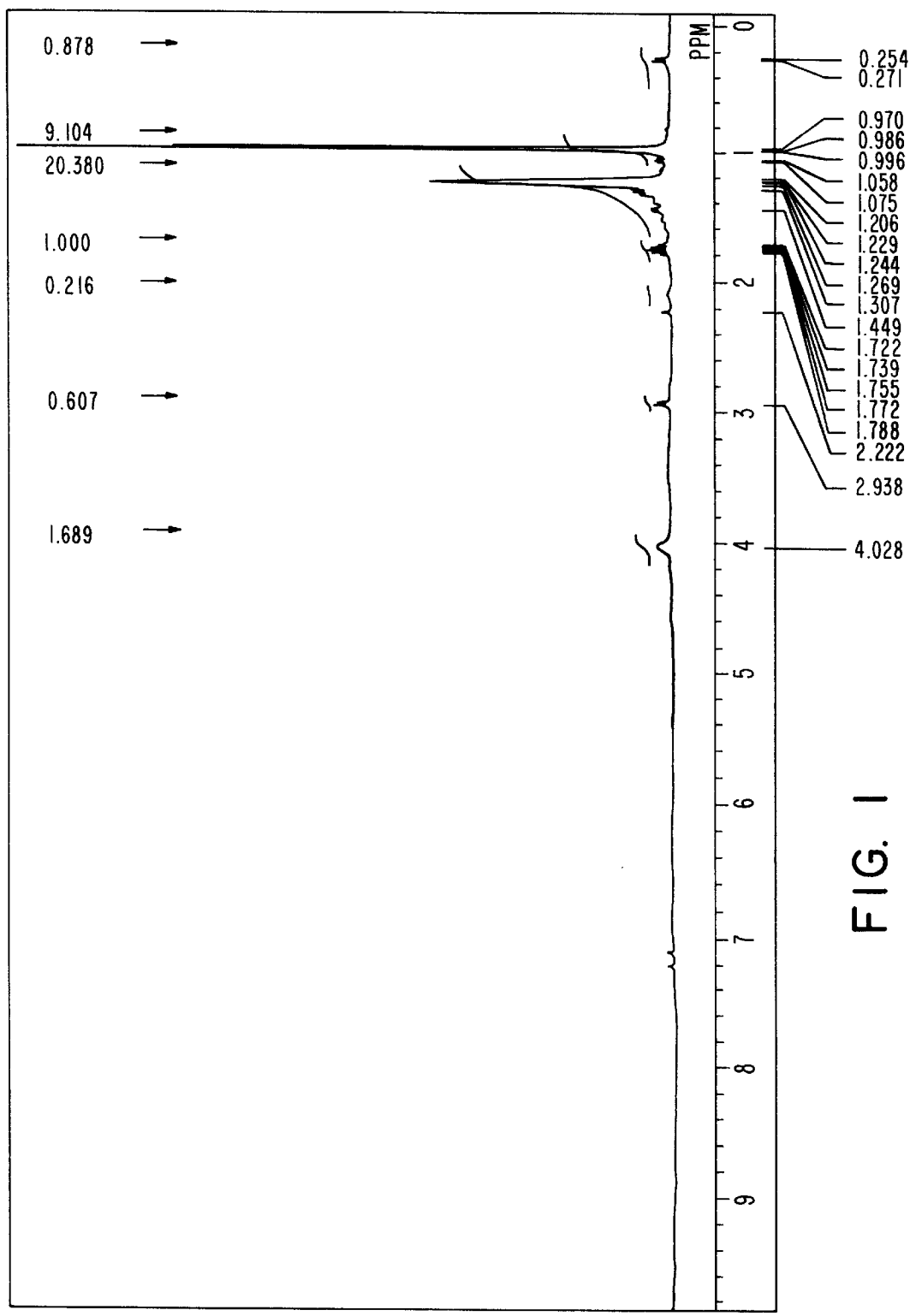
FIG. 1 is a chart showing an NMR spectrum of the reducing agent obtained in Reference Example 2.

Hereinafter, the present invention is illustrated in detail.

By the method for reducing α-aminoketones according to the present invention, the α-aminoalcohol derivatives of general formula (7) are produced from the α-aminoketone derivatives of general formula (1).

When, in the practice of the present invention, the α-aminoketone derivative of general formula (1) is an α-aminohaloketone derivative of the general formula (8);

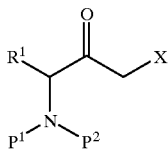

(8)

[wherein X represents a halogen atom; R¹ represents a substituted or unsubstituted allkyl group containing 1 to 20 carbon atoms, a substituted or unsubstituted aralkyl group containing 7 to 20 carbon atoms, a substituted or unsubstituted aryl group containing 6 to 20 carbon atoms, or a hydrogen atom; P¹ and P² each independently represents a hydrogen atom or an amino-protecting group, exclusive of the case where P¹ and P² are the same and each represents a hydrogen atom], an α-aminolialohydrin derivative of the general formula (9);

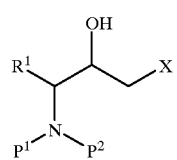

(9)

[wherein X, R¹, P¹ and P² are as defined above can be obtained as the α-aminoalcohol derivative of general formula (7).

The α-aminoalcohol derivatives of general formula (7) and the α-aminohalohydrin derivatives of general formula (9) are compounds useful as intermediates of medicinal compounds.

Referring to the α-aminoketone derivative of general formula (1) and to the α-aminohaloketone derivative of general formula (8), R¹ represents the side chain of a common α-amino acid, for example a protein-constituting amino acid, or the side chain of an α-amino acid derivative obtained by processing such a common α-amino acid and thus it represents a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms, or a hydrogen atom.

The substituent on said side chain is not limited to any particular species but includes, for example, a halogen atom, an allkoxycarbonyl group, an alkoxyl group, a protected amino group, a cyano group, a nitro group, a sulfinyl group, a sulfonyl group and an alkylthio group. Two or more such substituents may be introduced in the side chain.

Said substituted or unsubstituted alkyl group containing 1 to 20 carbon atoms is not limited to any particular species but includes, for example, methyl, ethyl, isopropyl, butyl, t-butyl, hydroxymethyl, mercaptomethyl, methylthiomethyl, and phenylthiomethyl. Said group preferably contains 1 to 10 carbon atoms.

Said substituted or unsubstituted aralkyl group containing 7 to 20 carbon atoms is not limited to any particular species but includes, for example, benzyl, p-hydroxybenzyl, p-methoxybenzyl, and α-phenylethyl.

Said group preferably contains 7 to 15 carbon atoms. Said substituted or unsubstituted aryl group containing 6 to 20 carbon atoms is not limited to any particular species but includes, for example, phenyl, naphthyl, p-hydroxyphenyl, p-nitrophenyl and p-chlorophenyl. Said group preferably contains 6 to 15 carbon atoms.

Referring to the α-aminoketone derivative of general formula (1), R² represents a group of the general formula (2) given above or a group of the general formula (3) given above.

Referring to the group of general formula (2), X represents a halogen atom and n represents an integer of 0 to 2.

Said halogen atom is not limited to any particular species but includes, for example, a chlorine atom, a bromine atom, an iodine atom and a fluorine atom. Preferred is a chlorine atom.

The group of general formula (2) is not limited to any particular species but includes, for example, chloromethyl, dichloromethyl, trichloromethyl, bromomethyl, dibromomethyl, tribromomethyl, fluoromethyl, difluoromethyl, trifluoromethyl, iodomethyl, diiodomethyl and triiodomethyl. Among them, chloromethyl, dichloromethyl and trichloromethyl are preferred.

Referring to the group of general formula (3), Y represents an alkoxyl group, an aralkyloxyl group, a substituted or unsubstituted amino group, or an alkylthio group.

Said alkoxyl group is not limited to any particular species but includes, for example, methoxy, ethoxy and t-butoxy. Said group preferably contains 1 to 10 carbon atoms.

Said aralkyloxyl group is not limited to any particular species but includes, for example, benzyloxyl and p-nitrobenzyloxyl. Said group preferably contains 7 to 20 carbon atoms.

Said substituted or unsubstituted amino group is not limited to any particular species but includes, for example, amino and dimethylamino.

Said alkylthio group is not limited to any particular species but includes, for example, methylthio and phenylthio.

The group of general formula (3) is not limited to any particular species but includes, for example, methoxycarbonyl, ethoxycarbonyl, benzyloxycarbonyl, t-butoxycarbonyl and carbamoyl. Among them, methoxycarbonyl and ethoxycarbonyl are preferred. Referring to the α-aminoketone derivative of general formula (1) and the α-aminohaloketone derivative of general formula (8), $P^1$ and $P^2$ each independently represents a hydrogen atom or an amino-protecting group, exclusive of the case where $P^1$ and $P^2$ are the same and each represents a hydrogen atom.

Said amino-protecting group is not limited to any particular species provided that it has a protective effect in the reduction reaction. As examples, there may be mentioned those protective groups described by Theodora W. Green in "Protective Groups in Organic Synthesis", 2nd edition, John Wiley & Sons, 1990, pp.309–384, for example ethoxycarbonyl, methoxycarbonyl, t-butoxycarbonyl, benzyloxycarbonyl, acetyl, tosyl and benzoyl. The protective group further includes the case where the amino-protecting group intramolecularly forms an oxazolinone or oxazolidinone ring. (3S)-Tetrahydrofuranyloxycarbonyl, 3-hydroxy-2-methylbenzoyl and the like are also within the range of choice of the protective group.

Referring to the α-aminohaloketone derivative of general formula (8), X represents a halogen atom.

Said halogen atom is not limited to any particular species but includes, for example, a chlorine atom, a bromine atom, all iodine atom and a fluorine atom. Among them, a chlorine atom is preferred.

The α-aminolketone derivative of general formula (1) is not limited to any particular species but includes, for example, 1(S)-benzyl-2-oxo-3,3-dichloropropylcarbainic acid t-butyl ester, 1(R)-benzyl-2-oxo-3,3-dichloropropylcarbamic acid t-butyl ester, 1(S)-benzyl-2-oxo-3,3,3-trichloropropylcarbamic acid t-butyl ester, 1(R)-benzyl-2-oxo-3,3,3-trichloropropylcarbamic acid t-butyl ester, 3(S)-(N-benzyloxycarbonylamino)-2-oxo-4-phenylbutyric acid methyl ester and 3(R)-(N-benzyloxycarbonylamino)-2-oxo-4-phenylbutyric acid methyl ester.

The α-aminohaloketone derivative of general formula (8) is not limited to any particular species but includes, for example, optically active (S)-(1-benzyl-3-chloro-2-oxopropyl)carbamic acid t-butyl ester, (R)-(1-benzyl-3-chloro-2-oxopropyl)carbamic acid t-butyl ester, (S)-(1-benzyl-3-chloro-2-oxopropyl)carbamic acid methyl ester, (R)-(1-benzyl-3-chloro-2-oxopropyl)carbamic acid methyl ester, (S)-(1-benzyl-3-chloro-2-oxopropyl)carbamic acid ethyl ester, (R)-(1-benzyl-3-chloro-2-oxopropyl)carbamic acid ethyl ester, (S)-(1-benzyl-3-chloro-2-oxopropyl) carbamic acid benzyl ester, (R)-(1-benzyl-3-chloro-2-oxopropyl)carbamic acid benzyl ester, (S)-(1-benzyl-3-chloro-2-oxopropyl)carbamic acid tetrahydrofuran-3(S)-yl ester, (R)-(1-benzyl-3-chloro-2-oxopropyl)carbamic acid tetrahydrofuran-3(S)-yl ester, (S)-(1-phenylthiomethyl-3-chloro-2-oxopropyl)carbamic acid benzyl (ester, (R)-(1-phenylthiomethyl-3-chloro-2-oxopropyl)carbamic acid benzyl ester, (S)-(1-phenylthiomethyl-3-chloro-2-oxopropyl) carbamic acid t-butyl ester, (R)-(1-phenylthiomethyl-3-chloro-2-oxopropyl)carbamic acid t-butyl ester, (S)-(1-phenylthiomethyl-3-chloro-2-oxopropyl)carbamic acid methyl ester, (R)-(1-phenylthiomethyl-3-chloro-2-oxopropyl)carbamic acid methyl ester, (S)-(1-phenylthiomethyl-3-chloro-2-oxopropyl)carbamic acid ethyl ester, (R)-(1-phenylthiomethyl-3-chloro-2-oxopropyl) carbamic acid ethyl ester, N-((1R)-3-chloro-2-oxo-1-[(phenylsulfanil)methyl]propyl)-3-hydroxy-2-methylbenzamide, and N-{(1S)-3-chloro-2-oxo-1-[(phenylsulfanil)methyl]propyl}-3-hydroxy-2-methylbenzamide.

Referring to the organoaluminum compound of general formula (4), $R^3$, $R^4$ and $R^5$ each independently represents a substituted or unsubstituted alkyl group containing 1 to 10 carbon atoms, or a hydrogen atom, on condition that at most one of $R^3$, $R^4$ and $R^5$ represents a hydrogen atom.

Said substituted or unsubstituted alkyl group containing 1 to 10 carbon atoms is not limited to any particular species but includes, for example, methyl, ethyl, n-propyl, isopropyl and isobutyl. Among them, ethyl and isobutyl are preferred.

The organoaluminum compound of general formula (4) is not limited to any particular species but includes, for example, diisobutylaluminum hydride, triisobutylaluminum and triethylaluminum. Among them, diisobutylaluminum hydride and truisobutylaluminum are preferred.

Referring to the sulfonic acid derivative of general formula (5), $R^6$ represents a substituted or unsubstituted alkyl group containing 1 to 10 carbon atoms, a substituted or unsubstituted aralkyl group containing 7 to 20 carbon atoms, or a substituted or unsubstituted aryl group containing 6 to 20 carbon atoms.

Said substituted or unsubstituted alkyl group containing 1 to 10 carbon atoms is not limited to any particular species but includes, for example, methyl, ethyl, isopropyl, n-butyl and trichloromethyl. Among them, methyl is preferred.

Said substituted or unsubstituted aralkyl group containing 7 to 20 carbon atoms is not limited to any particular species but includes, for example, benzyl and 3-phenyl-1-propyl. Said group preferably contains 7 to 15 carbon atoms.

Said substituted or unsubstituted aryl group containing 6 to 20 carbon atoms is not limited to any particular species but includes, for example, phenyl, p-methylphenyl, p-nitrophenyl, m-chlorophenyl and naphthyl. Said group preferably contains 6 to 15 carbon atoms.

The sulfonic acid derivative of general formula (5) is not limited to any particular species but includes, for example, methanesulfonic acid, benzenesulfonic acid, toluenesulfonic acid and camphorsulfonic acid. Among them, methanesulfonic acid is preferred.

Referring to the alcohol compound of general formula (6), $R^7$ represents a substituted or unsubstituted, primary or secondary alkyl group containing 1 to 20 carbon atoms or a substituted or unsubstituted, primary or secondary aralkyl group containing 7 to 20 carbon atoms.

Said substituted or unsubstituted, primary or secondary alkyl group containing 1 to 20 carbon atoms is not limited to any particular species but includes, for example, methyl, ethyl, isopropyl, secondary-butyl, cyclohexyl and 2,4-dimethyl-3-pentyl. Said group preferably contains 1 to 10 carbon atoms, and isopropyl and secondary-butyl are more preferred.

Said substituted or unsubstituted, primary or secondary aralkyl group containing 7 to 20 carbon atoms is not limited to any particular species but includes, for example, benzhydryl, benzyl, phenylpropyl, α-phenylethyl and p-methoxybenzyl. Said group preferably contains 7 to 15 carbon atoms, and benzhydryl is more preferred.

The alcohol compound of general formula (6) is not limited to any particular species but includes, for example, isopropannol, benzhydrol, secondary-butanol and cyclohexanol. Among them, isopropanol and benzhydrol are preferred.

The reducing agent to be used in accordance with the present invention can be prepared by reacting the organoaluminum compound of general formula (4) with the sulfonic acid derivative of general formula (5) and the alcohol compound of general formula (6).

Said reducing agent has very high reducing activity and can convert the α-aminoketone derivatives or α-aminohaloketone derivatives to hydroxy compounds such as α-aminohalohydrins or α-aminohydroxy esters with very high stereoselectivity under mild conditions without requiring heating or cooling to an extremely low temperature.

The addition amount of the organoaluminum compound of general formula (4), that of the sulfonic acid derivative of general formula (5) and that of the alcohol compound of general formula (6) may suitably be selected according to the carbonyl compound of general formula (1) to be reduced, the organoaluminum compound of general formula (4) selected, the sulfonic acid derivative of general formula (5) selected, the alcohol compound of general formula (6) selected, the temperature at which the reducing agent is prepared, and the procedure for preparing the reducing agent, among others. It is preferred, however, that those addition amounts are, on the equivalent basis, as follows.

Thus, the organoaluminum compound of general formula (4) is preferably used in an amount of 0.5 to 2 molar equivalents relative to the carbonyl compound of general formula (1).

The sulfonic acid derivative of general formula (5) is preferably used in an amount of 1 to 1.5 molar equivalents, more preferably 1 to 1.2 molar equivalents, relative to the organoaluminum compound of general formula (4).

The alcohol compound of general formula (6) is preferably used in an amount of 2 to 4 molar equivalents, more preferably 2 to 2.4 molar equivalents, relative to the organoaluminum compound of general formula (4).

In the reduction method according to the present invention, the possibility that the above-mentioned reducing agent has such basic structure as shown below is estimated to be high.

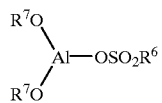

In the above formula, $R^6$ and $R^7$ are as defined above.

The formation of an active reducing species with a degree of association of the organoaluminum compound of not more than 3 is presumable as one of the factors enabling the reducing agent prepared in accordance with the present invention to show high reducing activity.

The method for reducing α-aminoketones according to the present invention can be carried out, for example, in the following manner. The reducing agent can be prepared by first mixing the organoaluminum compound of general formula (4) with the sulfonic acid derivative of general formula (5) in a solvent, such as toluene, benzene or xylene, preferably at −20° C. to 30° C., more preferably −10° C. to 25° C., and then adding benzhydrol as the alcohol compound of general formula (6), followed by stirring.

Then, the α-aminoketone derivative of general formula (1) is added to the reaction system, and the mixture is stirred for effecting the reduction of the α-aminoketone derivative of general formula (1). The order of addition of the compounds mentioned above is not necessarily limited to that mentioned above but may be changed unless the object of the invention is defeated. The reaction temperature preferably ranges from −20° C. to 30° C., more preferably −10 ° C. to 25° C.

The α-aminoketone derivative of general formula (1) as the starting material can be synthesized by various methods. For example, the α-aminohaloketone derivative of general formula (8) can generally be produced by reacting an α-amino acid derivative, such as an α-amino acid ester, with α-chloroacetic acid magnesium enolate (WO 96/23756), for instance.

In accordance with the present invention, the α-aminoketone derivatives can be reduced under mild conditions, without requiring an extremely low temperature or a high temperature, and very high stereoselectivity can be attained by adequately selecting the amino-protecting group, or by selecting the combination of the sulfonic acid of general formula (5) and the alcohol compound of general formula (6).

Said selection of the amino-protecting group can be made while taking the stereoselectivity of the reduction reaction into consideration. By using, as the amino-protecting group, an alkoxycarbonyl group such as methoxycarbonyl, t-butoxycarbonyl or ethoxycarbonyl or an aralkyloxycarbonyl group such as benzyloxycarbonyl, for instance, the reduction reaction can be allowed to proceed with high selectivity toward the erythro form.

Thus, for instance, by using methanesulfonic acid as the sulfonic acid of general formula (5) and benzhydrol as the alcohol compound of general formula (6), (S)-(1-benzyl-3-chloro-2-oxopropyl)carbamic acid t-butyl ester can be reduced with a very high diastereomer excess (d.e.) of not less than 97%.

Further, by using benzhydrol and such an α-aminoketoester derivative as (S)-(t-butoxycarbonyl-amino)-2-oxo-4-phenylbutyric acid methyl ester, the corresponding optically active α-hydroxy ester can be obtained with high erythro selectivity.

In this way, the α-aminoalcohol derivative of general formula (7) can be obtained stereoselectively in erythro isomer form from the α-aminoketone derivative of general formula (1). When the α-aminoketone derivative of general formula (1) is an α-aminohaloketone derivative of general formula (8), the erythro isomer of the α-aminohalohydrin derivative of general formula (9) can be obtained stereoselectively as the α-aminoalcohol derivative of general formula (7).

These compounds are all useful as intermediates of HIV protease inhibitors (Japanese Kokai Publication Hei-8-99959; Japanese Kokai Publication Hei-5-170722).

BEST MODE FOR CARRYING OUT THE INVENTION

The following examples illustrate the present invention in further detail. They are, however, by no means limitative of the scope of the present invention.

EXAMPLE 1

Production of 1(S)-benzyl-2(S)-hydroxy-chloropropyl]carbamic acid t-butyl ester (I)

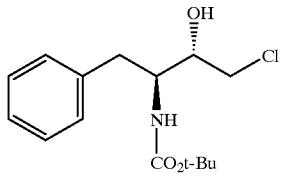

(I)

To a 0.95M hexane solution of triisobutylaluminum (12.7 ml; 12.1 mmol) was added 1.277 g (13.29 mmol) of methanesulfonic acid, and the mixture was stirred at room temperature for 2 hours. Then, 1.566 g (26.06 mmol) of isopropyl alcohol was added and the resultant mixture was stirred for 1 hour.

To the thus-prepared reducing agent was added a solution of 2.99 g (10.04 mmol) of [1(S)-benzyl-2-oxo-3-chloropropyl]carbamic acid t-butyl ester in 13.9 ml of toluene plus 5.6 ml of tetrahydrofuran, and the mixture was stirred at 25° C. for 4 hours. Hydrolysis with 10% sulfuric acid, extraction with ethyl acetate, drying and concentration gave 3.13 g of white crystals.

The crystals obtained were subjected to quantitative analysis by HPLC and the yields and selectivity were calculated.

HPLC analysis conditions:
Column: YMC-ODS A-303, 4.6×250 mm
Mobile phase: $CH_3CN/H_2O=45/55$
Flow rate: 1.0 ml/min.
Temperature: 30° C.
Retention time: (1S,2S) form –17 min.; (1S,2R) form –21 min.

Analysis of the crystals under the above conditions gave the following results.
[1(S)-benzyl-2(S)-hydroxy-3-chloropropyl]carbamic acid t-butyl ester: 2.829 g (9.44 mmol); yield 94.0%.
[1(S)-benzyl-2(R)-hydroxy-3-chloropropyl]carbamic acid t-butyl ester: 0.059 g (0.20 mmol); yield 2.0%.
Selectivity: (1S,2S) form/(1S,2R) form=98.0/2.0

EXAMPLE 2

Production of [1(S)-benzyl-2(S)-hydroxy-chloropropyl]carbamic acid t-butyl ester (I)

A 0.95M hexane solution of triisobutylaluminum (1.05 ml; 1.0 mmol) was diluted with 6 ml of toluene, then 100 mg (1.04 mmol) of methanesulfonic acid was added, and the mixture was stirred at room temperature for 30 minutes. Then, 393 mg (2.13 mmol) of benzhydrol was added, and the resultant mixture was stirred for 30 minutes.

To the thus-prepared reducing agent was added 298 mg (1.0 mmol) of [1(S)-benzyl-2-oxo-3-chloropropyl]carbamic acid t-butyl ester, and the mixture was stirred at 25° C. for 16 hours. Hydrolysis with 1 N hydrochloric acid, extraction with ethyl acetate, drying and concentration gave 300 mg of white crystals.

The crystals obtained were quantitatively analyzed by HPLC under the same conditions as used in Example 1, and the yields and selectivity were calculated.

Analysis of the crystals gave the following results.
[1(S)-benzyl-2(S)-hydroxy-3-chloropropyl]carbamic acid t-butyl ester: 278 mg (0.927 mmol); yield 92.6%.
[1(S)-benzyl-2(R)-hydroxy-3-chloropropyl]carbamic acid t-butyl ester: 3.1 mg (0.01 mmol); yield 1.0%.
Selectivity: (1S,2S) form/(1S,2R) form=98.9/1.1

EXAMPLE 3

Production of [1(S)-benzyl-2(S)-hydroxy-chloropropyl]carbamic acid methyl ester (II)

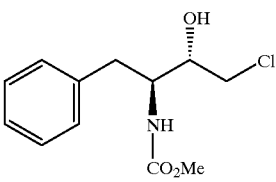

(II)

A 0.95M hexane solution of triisobutylaluminum (2.6 ml; 2.47 mmol) was diluted with 15 ml of toluene, then 250 mg (2.60 mmnol) of methanesulfonic acid was added, and the mixture was stirred at room temperature for 30 minutes. Then, 317 mg (5.27 mmol) of isopropyl alcohol was added, and the resultant mixture was stirred for 30 minutes.

To the thus-prepared reducing agent was added 620 mg (2.43 mmol) of [1(S)-benzyl-2-oxo-3-chloropropyl]carbamic acid methyl ester, and the mixture was stirred at 25° C. for 16 hours. Hydrolysis with 1 N hydrochloric acid, extraction with ethyl acetate, drying and concentration gave 631 mg of white crystals.

The crystals obtained were quantitatively analyzed by HPLC under the same conditions as used in Example 1, and the yields and selectivity were calculated.

Analysis of the crystals gave the following results.
[1(S)-benzyl-2(S)-hydroxy-3-chloropropyl]carbamic acid methyl ester: 580 mg (2.27 mmol); yield 93.6%.
[1(S)-benzyl-2(R)-hydroxy-3-chloropropyl]carbamic acid methyl ester: 22 mg (0.08 mmol); yield 3.5%.
Selectivity: (1S,2S) form/(1S,2R) form=96.4/3.6

EXAMPLE 4

Production of [1(R)-phenylthiomethyl-2(S)-hydroxy-3-chloropropyl]carbamic acid benzyl ester (III)

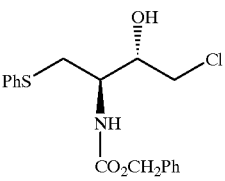

(III)

A 0.95M hexane solution of triisobutylaluminum (2.6 ml; 2.47 mmol) was diluted with 15 ml of toluene, then 242 mg (2.52 mmol) of methanesulfonic acid was added, and the mixture was stirred at room temperature for 30 minutes. Then, 296 mg (4.93 mmol) of isopropyl alcohol was added, and the resultant mixture was stirred for 30 minutes.

To the thus-prepared reducing agent was added 662 mg (2.42 mmol) of [1(R)-phenylthiomethyl-2(S)-hydroxy-3- chloropropyl]carbamic acid benzyl ester, and the mixture was stirred at 25° C. for 16 hours. Hydrolysis with 1N hydrochloric acid, extraction with ethyl acetate, drying and concentration gave 784 mg of pale yellow crystals.

The crystals obtained were quantitatively analyzed by HPLC under the same conditions as used in Example 1, and the yields and selectivity were calculated.

Analysis of the crystals gave the following results.
[1(R)-phenylthiomethyl-2(S)-hydroxy-3-chloropropyl] carbamic acid benzyl ester: 625 mg (2.27 mmol); yield 93.7%.
[1(R)-phenylthiomethyl-2(R)-hydroxy-3-chloropropyl] carbamic acid benzyl ester: 26 mg (0.09 mmol); yield 3.9%.
Selectivity: (1R,2S) form/(1R,2R) form=96.0/4.0

EXAMPLE 5

Production of [1(S)-benzyl-2(S)-hydroxy-3-chloropropyl]carbamic acid t-butyl ester (I)

A 0.95M hexane solution of triisobutylaluminum (1.05 ml; 1.0 mmol) was diluted with 6 ml of toluene, then 101 mg (1.05 mmol) of methanesulfonic acid was added, and the mixture was stirred at room temperature for 30 minutes. Then, 124 mg (2.07 mmol) of isopropyl alcohol was added, and the resultant mixture was stirred for 30 minutes.

To the thus-prepared reducing agent was added 298 mg (1.0 mmol) of [1(S)-benzyl-2-oxo-3-chloropropyl]carbamic acid t-butyl ester, and the mixture was stirred at 25° C. for 16 hours. After hydrolysis with 1 N hydrochloric acid, the reaction mixture was extracted with ethyl acetate.

The solution obtained was analyzed quantitatively by HPLC under the same conditions as used in Example 1, and the yields and selectivity were calculated.

Analysis of the solution gave the following results.
[1(S)-benzyl-2(S)-hydroxy-3-chloropropyl]-carbamic acid t-butyl ester: 290 mg (0.967 mmol); yield 96.8%.
[1(S)-benzyl-2(R)-hydroxy-3-chloropropyl]carbamic acid t-butyl ester: 5.5 mg (0.02 mmol); yield 1.8%.
Selectivity: (1S,2S) form/(1S,2R) form=98.1/1.9

EXAMPLE 6

Production of [1(S)-benzyl-2(S)-hydroxy-3-chloropropyl]carbamic acid t-butyl ester (I)

A 0.95M hexane solution of triisobutylaluminum (1.05 ml; 1.0 mmol) was diluted with 6 ml of toluene, then 202 mg (1.06 mmol) of p-toluenesulfonic acid hydrate was added, and the mixture was stirred at room temperature for 30 minutes. Then, 135 mg (2.25 mmol) of isopropyl alcohol was added, and the resultant mixture was stirred for 30 minutes.

To the thus-prepared reducing agent was added 299 mg (1.0 mmol) of [1(S)-benzyl-2-oxo-3-chloropropyl]carbamic acid t-butyl ester, and the mixture was stirred at 25° C. for 16 hours. After hydrolysis with 1 N hydrochloric acid, the reaction mixture was extracted with ethyl acetate.

The solution obtained was analyzed quantitatively by HPLC under the same conditions as used in Example 1, and the yields and selectivity were calculated.

Analysis of the solution gave the following results.
[1(S)-benzyl-2(S)-hydroxy-3-chloropropyl]carbamic acid t-butyl ester: 208 mg (0.69 mmol); yield 68.9%.
[1(S)-benzyl-2(R)-hydroxy-3-chloropropyl]carbamic acid t-butyl ester: 12.1 mg (0.04 mmol); yield 4.0%.
Selectivity: (1S,2S) form/(1S,2R) form=94.5/5.5

EXAMPLE 7

Production of [1 (S)-benzyl-2(S)-hydroxy-3-chlopropyl]carbamic acid t-butyl ester (I)

A 1.01M toluene solution of diisobutylaluminum hydride (1.0 ml; 1.01 mmol) was diluted with 6 ml of toluene, then 97.2 mg (1.01 mmol) of methanesulfonic acid was added, and the mixture was stirred at room temperature for 30 minutes. Then, 125 mg (2.08 mmol) of isopropyl alcohol was added, and the resultant mixture was stirred for 30 minutes.

To the thus-prepared reducing agent was added 301 mg (1.01 mmol) of [1(S)-benzyl-2-oxo-3-chloropropyl] carbamic acid t-butyl ester, and the mixture was stirred at 25° C. for 16 hours. After hydrolysis with 1 N hydrochloric acid, the reaction mixture was extracted with ethyl acetate.

The solution obtained was analyzed quantitatively by HPLC under the same conditions as used in Example 1, and the yields and selectivity were calculated.

Analysis of the solution gave the following results.
[I(S)-benzyl-2(S)-hydroxy-3-chloropropyl]carbamic acid t-butyl ester: 289 mg (0.96 mmol); yield 95.4%.
[1(S)-benzyl-2(R)-hydroxy-3-chloropropyl]carbamic acid t-butyl ester: 5.9 mg (0.02 mmol); yield 1.9%.
Selectivity: (1S,2S) form/(1S,2R) form=98.0/2.0

EXAMPLE 8

Production of (2S,3S)-3-[(t-butoxycarbonyl)amino]-2-hydroxy-4-phenylbutyricacid methyl ester (IV)

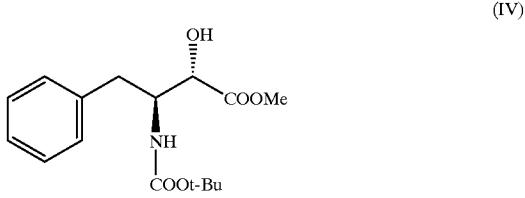

(IV)

A 1.01M toluene solution of diisobutylaluminum hydride (0.5 ml; 0.5 mmol) was diluted with 1 ml of toluene, the dilution was cooled on ice, then 50.8 mg (0.52 mmol) of methanesulfonic acid was added, and the mixture was stirred for 30 minutes. Then, 295 mg (1.56 mmol) of benzhydrol was added and, after allowing the mixture to return to room temperature, the mixture was stirred for 30 minutes.

To the thus-prepared reducing agent was added 81.0 mg (0.26 mmol) of (3S)-[(t-butoxycarbonyl)amino]-2-oxo-4-phenylbutyric acid methyl ester, and the mixture was stirred at room temperature for 5 hours. After hydrolysis with 1 N hydrochloric acid, the reaction mixture was extracted with ethyl acetate.

The solution obtained was analyzed quantitatively by HPLC under the same conditions as used in Example 1, and the yields and selectivity were calculated.

Analysis of the solution gave the following results.
(2S,3S)-3-[(t-butoxycarbonyl)amino]-2-hydroxy-4-phenylbutyric acid methyl ester: 53.3 mg (0.17 mmol); yield 66.3%.

(2R,3S)-3-[(t-butoxycarbonyl)amino]-2-hydroxy-4-phenylbutyric acid methyl ester: 3.4 mg (0.01 mmol); yield 4.2%.
Selectivity: (2S,3S) form/(2R,3S) form=94.0/6.0

Reference Example 1

Production of [1(S)-benzyl-2(S)-hydroxy-3-chloropropyl]carbamic acid t-butyl ester (I)

Triisopropoxyaluminum (200 mg, 0.98 mmol) was diluted with 6 ml of toluene. Thereto was added 285 mg (0.96 mmol) of [1(S)-benzyl-2-oxo-3-chloropropyl]carbamic acid t-butyl ester, and the mixture was stirred at 25° C. for 16 hours. After hydrolysis with 1N hydrochloric acid, the reaction mixture was extracted with ethyl acetate. The solution obtained was analyzed quantitatively by HPLC under the same conditions as used in Example 1 and the yields and selectivity were calculated.

Analysis of the solution gave the following results.
[1(S)-benzyl-2(S)-hydroxy-3-chloropropyl]carbamic acid t-butyl ester: 17 mg (0.06 mmol); yield 6.0%.
[1(S)-benzyl-2(R)-hydroxy-3-chloropropyl]carbamic acid t-butyl ester: 1.2 mg (0.004 mmol); yield 0.4%.
[1(S)-benzyl-2-oxo-3-chloropropyl]carbamic acid t-butyl ester: 246 mg (0.83 mmol); recovery 86.3%.
Selectivity: (1S,2S) form/(1S,2R) form 93.4/6.6

Reference Example 2

Triisobutylaluminum hydride (1M hexane solution; 1 ml, 1 mmol) was concentrated under reduced pressure. After argon substitution, the concentrate was diluted with 2 ml of deuterated toluene, and 0.064 ml (1 mmol) of methanesulfonic acid was further added. After 40 minutes, 0.23 ml (3 mmol) of isopropyl alcohol was added to give a reducing agent. After the lapse of 1 hour, the reducing agent was subjected to $^1$H-NMR spectrometry, whereby the chart shown in FIG. 1 was obtained.

EFFECT OF THE INVENTION

The present invention, which has the constitution mentioned above, makes it possible to produce aminohalohydrin derivatives, which are intermediates of useful medicinal compounds, from aminohaloketone derivatives under mild conditions and with high stereoselectivity.

What is claimed is:

1. A method for reducing α-aminoketones which comprises reacting an α-aminoketone derivative of the general formula (1);

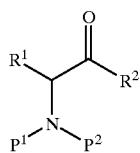

(1)

wherein $R^1$ represents one member selected from the group consisting of a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms, and a hydrogen atom; $R^2$ represents either a group of the general formula (2);

(2)

wherein X represents a halogen atom and n represents an integer of 0 to 2, or a group of the general formula (3);

(3)

wherein Y represents one member selected from the group consisting of an alkoxyl group, an aralkyloxyl group, a substituted or unsubstituted amino group, and an alkylthio group; $P^1$ and $P^2$ each independently represents a hydrogen atom or an amino-protecting group, exclusive of the case where $P^1$ and $P^2$ are the same and each represents a hydrogen atom, with a reducing agent prepared from an organoaluminum compound of the general formula (4);

(4)

wherein $R^3$, $R^4$ and $R^5$ each independently represents a substituted or unsubstituted alkyl group containing 1 to 10 carbon atoms, or a hydrogen atom, on condition that at most one of $R^3$, $R^4$ and $R^5$ represents a hydrogen atom, a sulfonic acid derivative of the general formula (5);

$$R^6SO_3H \qquad (5)$$

wherein $R^6$ represents one member selected from the group consisting of a substituted or unsubstituted alkyl group containing 1 to 10 carbon atoms, a substituted or unsubstituted aralkyl group containing 7 to 20 carbon atoms, and a substituted or unsubstituted aryl group containing 6 to 20 carbon atoms, and an alcohol compound of the general formula (6);

$$R^7OH \qquad (6)$$

wherein $R^7$ represents a substituted or unsubstituted, primary or secondary alkyl group containing 1 to 20 carbon atoms, or a substituted or unsubstituted, primary or secondary aralkyl group containing 7 to 20 carbon atoms, to give an α-aminoalcohol derivative of the general formula (7):

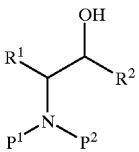

(7)

wherein $R^1$, $R^2$, $P^1$ and $P^2$ are as defined above.

2. The method for reducing α-aminoketones according to claim 1, wherein the sulfonic acid derivative of general formula (5) is methanesulfonic acid.

3. The method for reducing α-aminoketones according to claim 1, wherein the alcohol compound of general formula (6) is benzhydrol or isopropanol.

4. The method for reducing α-aminoketones according to claim 1, wherein the organoaluminum compound of general formula (4) is diisobutylaluminum hydride or triisobutylaluminum.

5. The method for reducing α-aminoketones according to claim 1, wherein the reduction reaction is carried out at temperatures of −20° C. to 30 ° C.

6. The method for reducing α-aminoketones according to claim 1, wherein the organoaluminum compound of general formula (4) is used in an amount of 0.5 to 2 moles per mole of the α-aminoketone derivative of general formula (1), the sulfonic acid derivative of general formula (5) in an amount of 1 to 1.5 moles per mole of the organoaluminum compound of general formula (4), and the alcohol compound of general formula (6) in an amount of 2 to 4 moles per mole of the organoaluminum compound of general formula (4).

7. The method for reducing α-aminoketones according to claim 1, wherein, in the α-aminoketone derivative of general formula (1), one of $P^1$ and $P^2$ is a hydrogen atom and the other is an amino-protecting group selected from among alkoxycarbonyl and aralkyloxycarbonyl groups.

8. The method for reducing α-aminoketones according to claim 1, wherein the α-aminoalcohol derivative of general formula (7) is obtained stereoselectively in the erythro isomer form.

9. The method for reducing α-aminoalcohols according to claim 1, wherein the α-aminoketone derivative of general formula (1) is an α-aminohaloketone derivative of the general formula (8);

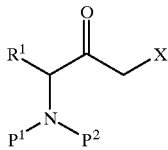

(8)

wherein X represents a halogen atom; $R^1$ represents one member selected from the group consisting of a substituted or unsubstituted alkyl group containing 1 to 20 carbon atoms, a substituted or unsubstituted aralkyl group containing 7 to 20 carbon atoms, a substituted or unsubstituted aryl group containing 6 to 20 carbon atoms, and a hydrogen atom; $P^1$ and $P^2$ each independently represents a hydrogen atom or an amino-protecting group, exclusive of the case where $P^1$ and $P^2$ are the same and each represents a hydrogen atom, and the α-aminoalcohol derivative of general formula (7) is an α-aminohalohydrin derivative of the general formula (9):

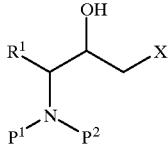

(9)

wherein X, $R^1$, $P^1$ and $P^2$ are as defined above.

10. The method for reducing α-aminoketones according to claim 9, wherein the α-aminohaloketone derivative of general formula (8) is one member selected from the group consisting of optically active (S)-(1-benzyl-3-chloro-2-oxopropyl)carbamic acid t-butyl ester, (R)-(1-benzyl-3-chloro-2-oxopropyl)carbamic acid t-butyl ester, (S)-(1-benzyl-3-chloro-2-oxopropyl)carbamic acid methyl ester, (R)-(1-benzyl-3-chloro-2-oxopropyl)carbamic acid methyl ester, (S)-(1-benzyl-3-chloro-2-oxopropyl)carbamic acid ethyl ester, (R)-(1-benzyl-3-chloro-2-oxopropyl)carbamic acid ethyl ester, (S)-(1-benzyl-3-chloro-2-oxopropyl)carbamic acid benzyl ester, (R)-(1-benzyl-3-chloro-2-oxopropyl)carbamic acid benzyl ester, (S)-(1-benzyl-3-chloro-2-oxopropyl)carbamic acid tetrahydrofuran-3(S)-yl ester, (R)-(1-benzyl-3-chloro-2-oxopropyl)carbamic acid tetrahydrofuran-3(S)-yl ester, (S)-(1-phenylthiomethyl-3-chloro-2-oxopropyl)carbamic acid benzyl ester, (R)-(1-phenylthiomethyl-3-chloro-2-oxopropyl)carbamic acid benzyl ester, (S)-(1-phenylthiomethyl-3-chloro-2-oxopropyl)carbamic acid t-butyl ester, (R)-(1-phenylthiomethyl-3-chloro-2-oxopropyl)carbamic acid t-butyl ester, (S)-(1-phenylthiomethyl-3-chloro-2-oxopropyl)carbamic acid methyl ester, (R)-(1-phenylthiomethyl-3-chloro-2-oxopropyl)carbamic acid methyl ester, (S)-(1-phenylthiomethyl-3-chloro-2-oxopropyl)carbamic acid ethyl ester, (R)-(1-phenylthiomethyl-3-chloro-2-oxopropyl)carbamic acid ethyl ester, N-{(1R)-3-chloro-2-oxo-1-[(phenylsulfanil)methyl]propyl}-3-hydroxy-2-methylbenzamide, and N-{(1S)-3-chloro-2-oxo-1-[(phenylsulfanil)methyl]propyl}-3-hydroxy-2-methylbenzamide.

11. The method for reducing α-aminoketones according to claim 2, wherein the alcohol compound of general formula (6) is benzhydrol or isopropanol.

12. The method for reducing α-aminoketones according to claim 2, wherein the organoaluminum compound of general formula (4) is diisobutylaluminum hydride or tri-isobutylaluminum.

13. The method for reducing α-aminoketones according to claim 3, wherein the organoaluminum compound of general formula (4) is diisobutylaluminum hydride or tri-isobutylaluminum.

14. The method for reducing α-aminoketones according to claim 2, wherein the reduction reaction is carried out at temperatures of −20° C. to 30° C.

15. The method for reducing α-aminoketones according to claim 3, wherein the reduction reaction is carried out at temperatures of −20° C. to 30° C.

16. The method for reducing α-aminoketones according to claim 4, wherein the reduction reaction is carried out at temperatures of −20° C. to 30° C.

17. The method for reducing α-aminoketones according to claim 2, wherein the organoaluminum compound of general formula (4) is used in an amount of 0.5 to 2 moles per mole of the α-aminoketone derivative of general formula (1) the sulfonic acid derivative of general formula (5) in an amount of 1 to 1.5 moles per mole of the organoaluminum compound of general formula (4), and the alcohol compound of general formula (6) in an amount of 2 to 4 moles per mole of the organoaluminum compound of general formula (4).

18. The method for reducing α-aminoketones according to claim 3, wherein the organaluminum compound of general formula (4) is used in an amount of 0.5 to 2 moles per mole of the α-aminoketone derivative of general formula (1), the sulfonic acid derivative of general formula (5) in an amount of 1 to 1.5 moles per mole of the organoaluminum compound of general formula (4), and the alcohol compound of general formula (6) in an amount of 2 to 4 moles per mole of the organoaluminum compound of general formula (4).

19. The method for reducing α-aminoketones according to claim 4, wherein the organoaluminum compound of general formula (4) is used in an amount of 0.5 to 2 moles per mole of the α-aminoketone derivative of general formula (1), the sulfonic acid derivative of general formula (5) in an amount of 1 to 1.5 moles per mole of the organoaluminum compound of general formula (4), and the alcohol compound of general formula (6) in an amount of 2 to 4 moles per mole of the organoaluminum compound of general formula (4).

20. The method for reducing α-aminoketones according to claim 5, wherein the organoaluminum compound of general formula (4) is used in an amount of 0.5 to 2 moles per mole of the α-aminoketone derivative of general formula (1), the sulfonic acid derivative of general formula (5) in an amount of 1 to 1.5 moles per mole of the organoaluminum compound of general formula (4), and the alcohol compound of general formula (6) in an amount of 2 to 4 moles per mole of the organoaluminum compound of general formula (4).

* * * * *